(12) United States Patent
Stelzig et al.

(10) Patent No.: US 9,849,209 B2
(45) Date of Patent: Dec. 26, 2017

(54) ABSORBENT STRUCTURES AND CORES WITH EFFICIENT IMMOBILIZATION OF ABSORBENT MATERIAL

(71) Applicant: The Procter & Gamble Company, Cincinnati, OH (US)

(72) Inventors: Lutz Stelzig, Frankfurt (DE); Hans Adolf Jackels, Mechernich (DE); Thomas Jarke, Frankfurt (DE); Thorsten Rinnert, Fernwald (DE)

(73) Assignee: The Procter & Gamble Company, Cincinnati, OH (US)

( * ) Notice: Subject to any disclaimer, the term of this patent is extended or adjusted under 35 U.S.C. 154(b) by 587 days.

(21) Appl. No.: 14/561,241

(22) Filed: Dec. 5, 2014

(65) Prior Publication Data

US 2015/0174280 A1     Jun. 25, 2015

(30) Foreign Application Priority Data

Dec. 19, 2013    (EP) .................................... 13198419

(51) Int. Cl.
*A61F 13/532*     (2006.01)
*A61F 13/535*     (2006.01)
(Continued)

(52) U.S. Cl.
CPC ........ *A61L 15/22* (2013.01); *A61F 13/15617* (2013.01); *A61F 13/15658* (2013.01);
(Continued)

(58) Field of Classification Search
CPC .......... A61F 13/15617; A61F 13/15658; A61F 13/15707; A61F 13/53; A61F 13/532;
(Continued)

(56) References Cited

U.S. PATENT DOCUMENTS 3,848,594 A    11/1974    Buell
3,860,003 A    1/1975    Buell
(Continued)

FOREIGN PATENT DOCUMENTS

EP            2532331        12/2012
WO      WO 95/34329      12/1995
(Continued)

OTHER PUBLICATIONS

International Search Report, PCT/US2014/070250, dated Mar. 11, 2015, 10 pages.

*Primary Examiner* — Susan Su
(74) *Attorney, Agent, or Firm* — Wednesday G. Shipp

(57) ABSTRACT

An absorbent structure comprising a planar substrate, an auxiliary glue applied on the substrate, an absorbent material comprising from 80% to 100% by weight of superabsorbent particles deposited on the substrate on an absorbent material deposition area comprising a pattern of absorbent material land areas separated by absorbent material-free junction areas, wherein the deposition area can be notionally divided in eight deposition zones of equal length along the longitudinal direction. A fibrous thermoplastic adhesive layer immobilizes at least some of the absorbent material. The absorbent material is profiled along the longitudinal direction so that at least one of the eight deposition zones is a zone of lower absorbent material amount and the auxiliary glue is absent, or present at a level of at least 50% by weight lower than the average amount of auxiliary glue in at least one of these zones of lower absorbent material amount.

19 Claims, 8 Drawing Sheets

(51) Int. Cl.
  *A61L 15/22* (2006.01)
  *A61F 13/534* (2006.01)
  *A61F 13/15* (2006.01)
  *A61F 13/53* (2006.01)
  *A61L 15/58* (2006.01)
  *A61L 15/60* (2006.01)

(52) U.S. Cl.
  CPC ........ *A61F 13/15707* (2013.01); *A61F 13/53* (2013.01); *A61F 13/532* (2013.01); *A61F 13/534* (2013.01); *A61F 13/535* (2013.01); *A61L 15/58* (2013.01); *A61L 15/60* (2013.01); *A61F 2013/530481* (2013.01); *Y10T 428/24851* (2015.01)

(58) Field of Classification Search
  CPC .................. A61F 13/534; A61F 13/535; A61F 2013/530481; A61F 13/1565; A61F 13/15666; A61F 13/4755; A61F 2013/5315; A61F 2013/53472
  USPC .................................................. 604/358–392
  See application file for complete search history.

(56) References Cited

U.S. PATENT DOCUMENTS

| | | | |
|---|---|---|---|
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,609,518 A | 9/1986 | Curro et al. | |
| 4,629,643 A | 12/1986 | Curro et al. | |
| 4,662,875 A | 5/1987 | Hirotsu et al. | |
| 4,681,793 A | 7/1987 | Linman et al. | |
| 4,695,278 A | 9/1987 | Lawson | |
| 4,699,622 A | 10/1987 | Toussant et al. | |
| 4,710,189 A | 12/1987 | Lash | |
| 4,731,066 A | 3/1988 | Korpman | |
| 4,785,996 A | 11/1988 | Ziecker et al. | |
| 4,795,454 A | 1/1989 | Dragoo | |
| 4,808,178 A | 2/1989 | Aziz et al. | |
| 4,842,666 A | 6/1989 | Werenicz | |
| 4,846,815 A | 7/1989 | Scripps | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 5,006,394 A | 4/1991 | Baird | |
| 5,137,537 A | 8/1992 | Herron et al. | |
| 5,151,092 A | 9/1992 | Buell et al. | |
| 5,221,274 A | 6/1993 | Buell et al. | |
| 5,242,436 A | 9/1993 | Weil et al. | |
| 5,433,715 A | 7/1995 | Tanzer et al. | |
| 5,499,978 A | 3/1996 | Buell et al. | |
| 5,507,736 A | 4/1996 | Clear et al. | |
| 5,549,791 A | 8/1996 | Herron et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,414 A | 3/1997 | Richards et al. | |
| 5,607,760 A | 3/1997 | Roe | |
| 5,609,587 A | 3/1997 | Roe | |
| 5,643,588 A | 7/1997 | Roe et al. | |
| 5,700,254 A | 12/1997 | McDowall et al. | |
| H1732 H | 6/1998 | Johnson | |
| 5,865,823 A | 2/1999 | Curro | |
| 5,938,648 A | 8/1999 | LaVon et al. | |
| 5,968,025 A | 10/1999 | Roe et al. | |
| 6,004,306 A | 12/1999 | Robles et al. | |
| 6,534,149 B1 | 3/2003 | Daley et al. | |
| 6,632,504 B1 | 10/2003 | Gillespie et al. | |
| 6,645,569 B2 | 11/2003 | Cramer et al. | |
| 6,716,441 B1 | 4/2004 | Osborne et al. | |
| 6,863,933 B2 | 3/2005 | Cramer et al. | |
| 6,946,585 B2 | 9/2005 | London Brown | |
| 7,112,621 B2 | 9/2006 | Rohrbaugh et al. | |
| 7,744,576 B2 | 6/2010 | Busam et al. | |
| 2002/0123728 A1 | 9/2002 | Graef et al. | |
| 2003/0148684 A1 | 8/2003 | Cramer et al. | |
| 2005/0008839 A1 | 1/2005 | Cramer et al. | |
| 2005/0101929 A1* | 5/2005 | Waksmundzki .. A61F 13/15658 604/378 |
| 2006/0024433 A1 | 2/2006 | Blessing et al. | |
| 2006/0048880 A1* | 3/2006 | Blessing ........... A61F 13/15658 156/60 |
| 2006/0178071 A1 | 8/2006 | Schmidt et al. | |
| 2007/0093767 A1 | 4/2007 | Carlucci et al. | |
| 2007/0118087 A1 | 5/2007 | Flohr et al. | |
| 2008/0091159 A1 | 4/2008 | Carlucci et al. | |
| 2008/0312617 A1 | 12/2008 | Hundorf et al. | |
| 2008/0312619 A1 | 12/2008 | Ashton et al. | |
| 2008/0312622 A1 | 12/2008 | Hundorf et al. | |
| 2009/0318884 A1 | 12/2009 | Meyer et al. | |
| 2010/0051166 A1 | 3/2010 | Hundorf et al. | |
| 2011/0250413 A1 | 10/2011 | Lu et al. | |
| 2011/0268932 A1 | 11/2011 | Catalan et al. | |
| 2011/0319846 A1 | 12/2011 | Rinnert et al. | |
| 2011/0319848 A1 | 12/2011 | McKiernan et al. | |
| 2012/0316524 A1 | 12/2012 | Thomann et al. | |
| 2012/0316526 A1 | 12/2012 | Rosati et al. | |
| 2012/0316527 A1 | 12/2012 | Rosati et al. | |
| 2012/0316528 A1 | 12/2012 | Kreuzer et al. | |
| 2012/0316529 A1 | 12/2012 | Kreuzer et al. | |
| 2013/0331806 A1 | 12/2013 | Rosati et al. | |
| 2014/0005622 A1 | 1/2014 | Wirtz et al. | |
| 2015/0038929 A1* | 2/2015 | Van Malderen .... A61F 13/5323 604/370 |
| 2015/0342796 A1* | 12/2015 | Bianchi ............. A61F 13/51108 604/370 |

FOREIGN PATENT DOCUMENTS

| | | |
|---|---|---|
| WO | 2004/071539 | 8/2004 |
| WO | WO 2009/155265 | 12/2009 |
| WO | WO 2012/052172 | 4/2012 |
| WO | WO 2013/108863 | 7/2013 |
| WO | WO 2013/184859 | 12/2013 |
| WO | WO 2014/004283 | 1/2014 |

* cited by examiner

ABSORBENT STRUCTURES AND CORES WITH EFFICIENT IMMOBILIZATION OF ABSORBENT MATERIAL

FIELD OF THE INVENTION

The invention relates to absorbent structures and absorbent cores that can be used in personal hygiene articles such as, but not limited to, baby diapers, training pants, feminine pads or adult incontinence products.

BACKGROUND OF THE INVENTION

Absorbent articles for personal hygiene, such as baby diapers, training pants for toddlers, feminine pads and adult incontinence undergarments, are designed to absorb and contain body exudates, in particular large quantity of urine. These absorbent articles comprise several layers providing different functions, for example a topsheet, a backsheet and an absorbent core positioned between the topsheet and backsheet, among other layers. The key functions of the absorbent core are to absorb and retain the exudates for a prolonged period of time, for example overnight for a diaper, to minimize re-wet to keep the wearer dry and to avoid soiling of clothes or bed sheets.

The majority of currently marketed absorbent articles comprise as absorbent material a blend of comminuted wood pulp with superabsorbent polymers (SAP) in particulate form, also called absorbent gelling materials (AGM), for example as disclosed in U.S. Pat. No. 5,151,092 (Buell). The SAP provides most of the absorbent capacity while the cellulose fibers can serve to immobilize the SAP within the core. Absorbent cores consisting essentially of SAP without cellulose fibers (also airfelt-free cores) have been proposed for example in WO2004/071539 (Busam), WO2008/155699 (Hundorf), WO95/11652 (Tanzer) or WO2012/052172 (Van Malderen). Removing the cellulose fibers has the advantage of providing thinner cores, but creates new challenges in terms of immobilization of the SAP in dry and wet state. This problem has been addressed in Busam and Hundorf by spraying a fiberized hot-melt thermoplastic material on a discontinuous SAP layer. These documents also consider using an auxiliary glue to improve the adhesion of the thermoplastic material to the substrate layer. More recently, WO2010/027719 (Hundorf) disclosed an improved process for making such cellulose free absorbent core using a plurality of cross-bars.

There is a continuous need for providing improved absorbent cores that balance absorbency performance with material saving. The present invention provides an improvement to the previously proposed cores having little or no cellulose fibers. The absorbent structures and cores of the invention have a profiled absorbent material distribution to provide higher amount of absorbent material where it is most needed, typically towards the crotch and to a lesser extent front of the absorbent structure or core, while eliminating or at least substantially reducing the auxiliary glue in the zones having low amount of absorbent material, typically towards the back of the absorbent structure and/or towards the front of the structure. This combination of features provides a reduction of adhesive usage while maintaining high absorbency performance and good dry and wet SAP immobilization properties.

SUMMARY OF THE INVENTION

The present invention is, in a first aspect, for an absorbent structure as indicated in the claims. The structure comprises a substantially planar substrate extending in a transversal directions (x) and a longitudinal direction (y), an auxiliary glue applied directly over the substrate on an auxiliary glue application area, an absorbent material deposited on the substrate in a pattern comprising absorbent material land areas separated by absorbent material-free junction areas, the periphery of the pattern defining an absorbent material deposition area, and a fibrous thermoplastic adhesive layer which covers at least some of the land areas and the absorbent material-free junction areas to thereby immobilize at least some of the absorbent material on the substrate. The absorbent material comprises from 80% to 100% by weight of superabsorbent particles.

The absorbent material deposition area can be notionally divided in eight zones of equal length along the longitudinal direction of the structure. The absorbent material is profiled along the longitudinal direction of the structure so that at least one of the eight deposition zones is a zone of lower absorbent material amount, hereby defined as having an amount of absorbent material that is at least 20% by weight lower than the average amount of absorbent material in the eight deposition zones (which together forms the absorbent material deposition area). The auxiliary glue is absent, or present at a level of at least 50% lower than the average amount of auxiliary glue in the eight deposition zones, in at least one of these deposition zones of lower absorbent material amount.

In a second aspect, the absorbent structure can be combined with a second substrate, which can also be part of a second absorbent structure, to form an absorbent core, as indicated in the claims, wherein the first substrate and the second substrate together form a core wrap that encloses the absorbent material. The absorbent core may be used in a wide range of absorbent articles in particular diapers and training pants. In a further aspect, the invention is for a method of making the absorbent structure and the absorbent core of the invention.

The invention can be described in a simplified way as an absorbent structure having a longitudinally profiled distribution of superabsorbent particles which are immobilized by a fibrous thermoplastic adhesive layer and an auxiliary glue. The auxiliary glue is not applied or applied at a lower amount in the zones having a relatively low amount of superabsorbent material. The invention allows to limit the usage of auxiliary glue to the zones where it is most needed, resulting in material cost saving and in some cases improving liquid handling.

DETAILED DESCRIPTION OF THE INVENTION

Introduction

Figure 1:
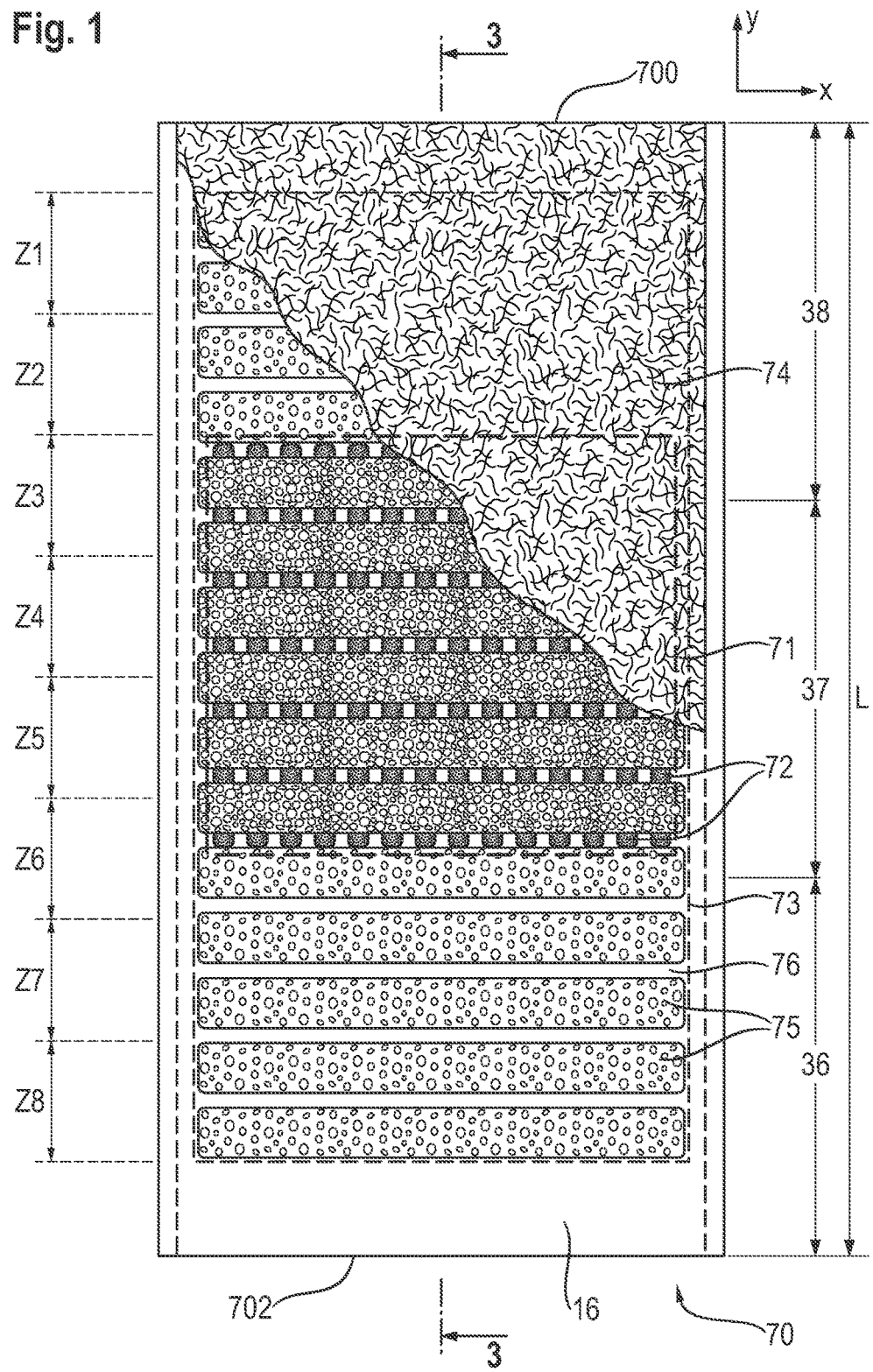
FIG. 1 is a top view of an absorbent structure according to the invention with the fibrous thermoplastic adhesive layer partially removed.
Figure 2:
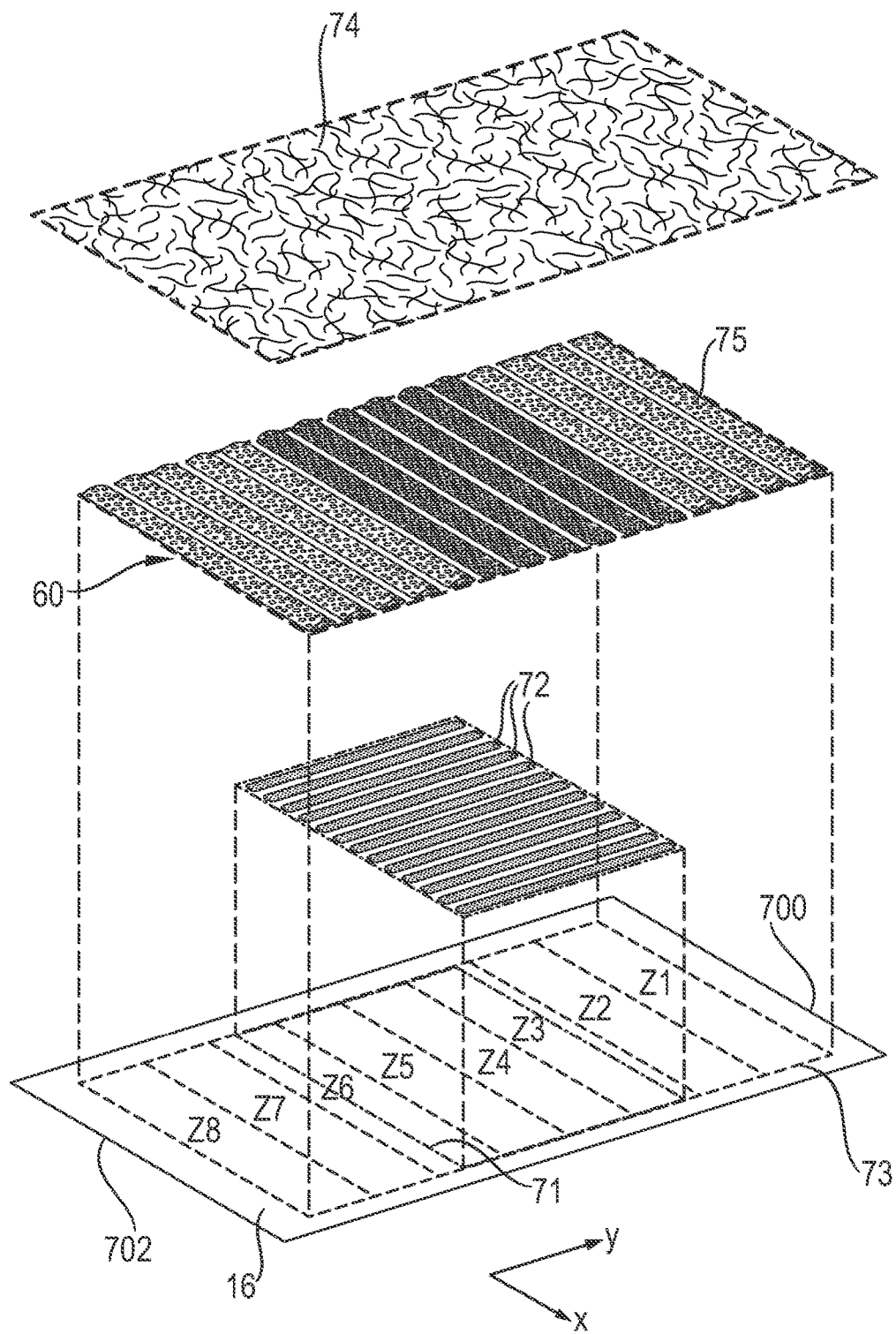
FIG. 2 is an exploded perspective view of the structure of FIG. 1.
Figure 3:
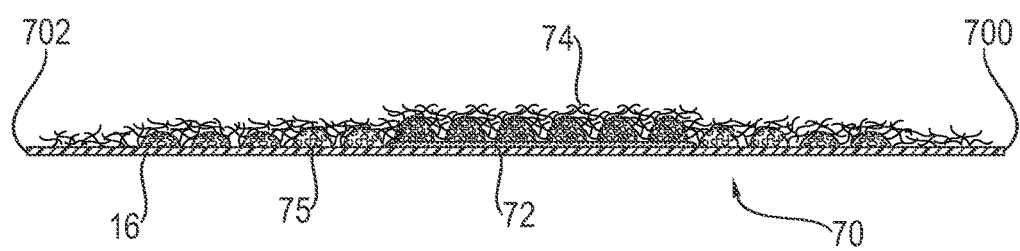
FIG. 3 is a cross-section view of the absorbent structure of FIG. 1 along the longitudinal direction.

In a first aspect, the present invention is for an absorbent structure 70 as exemplarily illustrated in FIG. 1-3. The absorbent structure may be used to make an absorbent core 28 as exemplarily illustrated in FIG. 4-7, which may be incorporated in an absorbent article as exemplarily shown in FIG. 12. The absorbent cores of the invention comprise at least one absorbent structure as claimed, and a second substrate to form a core wrap enclosing the absorbent material and optionally further components. In particular an absorbent core may be formed by combining two absorbent structures according to the invention, where the respective absorbent material land areas and junction areas are offset relative to each other so that a substantially continuous absorbent material layer is formed in the absorbent core.

As used herein, the term "absorbent article" refers to disposable products such as infant diapers (as exemplarily shown on FIG. 12), feminine pads, training pants, adult incontinence products and the like which are placed against or in proximity to the body of a wearer to absorb and contain the various exudates discharged from the body. Typically absorbent articles comprise a topsheet, a backsheet, an absorbent core and optionally an acquisition layer and/or distribution layer, and other components, with the absorbent core normally placed between the backsheet and the acquisition system or topsheet. The absorbent core is typically the component of the absorbent article which comprises all, or at least the majority of, the superabsorbent polymer (SAP) and has the most absorbent capacity of all the components of the absorbent article. The absorbent core typically comprises an absorbent material enclosed in a core wrap formed by two substrates.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Unless indicated otherwise, the description refers to the absorbent structure, core and article before use (i.e. dry, and not loaded with a fluid) and conditioned at least 24 hours at 21° C.+/−2° C. and 50+/−20% Relative Humidity (RH).

The absorbent structures, cores and articles of the invention will be further generally below and by way of illustration with the embodiments exemplarily shown in the Figures, which are not considered limiting the scope of the invention unless indicated otherwise.

Absorbent Structure 70

FIG. 1 shows a schematic top view of an absorbent structure 70 according to the invention with the fibrous thermoplastic adhesive layer 74 partially removed to better show the underlying absorbent material pattern of land areas 75 and absorbent material-free junction areas 76, the auxiliary glue 72 and the substrate 16. These individual components and their relations are further discussed below. The absorbent structure has a front edge 700 and a back edge 702. The front edge is the edge of the structure intended to be placed towards the front of the article when the absorbent structure has been integrated in an absorbent article. The back edge is the edge of the structure opposite the front edge. In case of doubt, the front edge may be in general towards the side of the structure with the most absorbent material. The length L of the substrate is measured along the longitudinal direction between the front and back edges. The structure can be virtually divided in three thirds, a front third 38 starting from the font edge 700, a back third 36 starting from the back edge 702 and a central third in-between, each third defined has having a length of a third of L (L/3), as shown in FIG. 1.

Substrate 16

The substrate 16 is substantially planar and extends in a transversal direction (x) and a longitudinal direction (y). By substantially planar it is meant that the substrate can be laid flat on a surface. However, the substrate used can typically be a thin web of material of the nonwoven type which is conformable and can also be laid on a non flat surface for example a drum during the making process of the absorbent structure or rolled and stored as a roll of stock material before being converted into an absorbent structure. The substrate may also be folded during its processing for example to form a C-wrap longitudinal side seal around a second substrate to enclose the absorbent material, as will be discussed further below. For ease of discussion, the substrate is represented in FIG. 1 in a flat state and extending in a transversal direction (x) and a longitudinal direction (y). The substrate can typically be generally rectangular with a width W in the transversal direction and a length L in the longitudinal direction. The width and length of the substrate may vary depending on the intended usage. For baby and infant diapers, the width and length of the core may for example be in the range from 40 mm to 200 mm for the width and 100 to 500 mm for the length.

The substrate 16 may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932 A1, US 2011/0319848 A1 and US 2011/0250413 A1. Nonwoven materials provided from synthetic fibers may be used, such as PE, PET and in particular PP.

As used herein, the terms "nonwoven layer" or "nonwoven web" generally means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as melt-blowing, spunbonding, solvent spinning, electrospinning, carding and airlaying. The basis weight of nonwoven webs is usually expressed in grams per square meter (g/m$^2$ or gsm).

The substrate may typically be commercially supplied as a roll of material web of several hundred meters of length. The roll is then integrated in a converting line and unrolled at high speed while the auxiliary glue, the absorbent material and the fibrous thermoplastic adhesive layer are applied on or deposited over the substrate and then further converted into an absorbent core by enclosing the absorbent material in a core wrap together with a second substrate. Typically the machine direction (MD) of the converting line may correspond to the longitudinal direction (y) of the substrate and the cross-machine direction (CD) to the transversal direction (x) of the substrate. The absorbent structures and/or cores may thus be typically formed cores continuously and the structures and/or cores individualized by cutting them along their transversal edges 700, 702. This will be further exemplarily discussed in the process section further below.

Auxiliary Glue 72

An auxiliary glue 72 is applied directly over the substrate 16 on an auxiliary glue application area 71. The auxiliary glue may improve the adhesion between the first substrate 16 and both the absorbent material (in the absorbent material land areas 75) and the fibrous thermoplastic material 74 (in the absorbent material-free junction areas 76). The auxiliary glue may be for example any kind of thermoplastic hot-melt adhesives used in the field of absorbent core making. Such an adhesive generally includes one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.), a resin or analogous material (sometimes called a tackifier) to provide adhesive strength (e.g., hydrocarbons distilled from petroleum distillates; rosins and/or rosin esters; terpenes derived, for example, from wood or citrus, etc.); and optional waxes, plasticizers or other materials to modify viscosity (e.g., mineral oil, polybutene, paraffin oils, ester oils, and the like), and/or other additives including, but not limited to, antioxidants or other stabilizers. The same raw material as those discussed below in details for the fibrous thermoplastic adhesive layer 74 may in particular be used, an exemplary commercial adhesive being available from Fuller under code 1286 or 1358.

The auxiliary glue can be applied on the substrate by any adhesive applicator known in the field, in particular bead, slot or spray nozzles. The auxiliary glue may be in principle applied as a continuous film on the whole of the auxiliary glue application area 71, however this may unduly increase the usage of adhesive material. The adhesive may thus be advantageously applied discontinuously to maximize the area covered with a lower amount of adhesive. The auxiliary glue may thus be applied as a relatively wide curtain of adhesive using as a spray nozzle. The auxiliary glue may also be applied discontinuously as a pattern of discrete application zones within the application area 72. For example, the auxiliary glue can be applied using a slot coating process as a pattern comprising a plurality of spaced-apart slots which may each extend in the longitudinal direction, as represented in FIGS. 1-2 by the slots 72. The slots may for example have a width of from 0.5 mm to 3 mm, and/or have a transversal spacing therebetween of from 0.5 mm to 4 mm. The slots may all be of equal length as represented in FIG. 1, but may also have varying length. For example if the absorbent material was also profiled transversally with more material towards the transversal center of the substrate, it may be beneficial to have longer or wider slots towards this center of the substrate. In the example of FIG. 1, the absorbent material is not profiled in the transversal direction. The adhesive material slots 72 in this example are regularly spaced and all have the same length and width. Each slot may be applied continuously in the longitudinal direction as represented in FIG. 1 but they may also be applied discontinuously. The slots may all have the same length or may have different lengths, in case more immobilization was requested in some areas. When applied as slots, the auxiliary glue 72 in the slots may for example be applied at a basis weight in the range from 1 gsm to 20 gsm, in particular from 2 gsm to 10 gsm, for example 3 or 4 gsm. More generally, considering the auxiliary glue application 71 as a whole, with any areas free of glue between the slots or any areas free of glue within for example the lines of a spiral glue application, the basis weight over the whole application area may for example be half the basis weight indicated above for the slots 72. The basis weight may also vary locally within the auxiliary glue application area 71.

The "auxiliary glue application area" as used herein means the smallest area 71 in the plane of the substrate whose periphery encompasses the auxiliary glue, including any areas free of adhesive between any discrete auxiliary glue application zones if present. In the example of FIG. 1, this is a rectangular area which encompasses the slots 72 as well as the areas between the slots. The auxiliary glue application area 71 may have any shape adapted to the intended usage of the absorbent article and the distribution of absorbent material. In particular, the auxiliary glue application area may be rectangular, shaped with a tapering in the central region of the substrate, or with a central elongated portion and shorter side portions. It is also possible that the auxiliary glue application area comprise separated sub-areas. A sub-area is hereby defined as an adhesive application area separated from another by more than 10 mm. In that case the adhesive free area between the adhesive application sub-areas is not considered to be part of the auxiliary glue application area, for example for the determination of the basis weight of the auxiliary glue. Alternative shapes and positions of the area 71 are exemplified in FIGS. 8-11 discussed further below.

Absorbent Material

The absorbent material comprises a relative high amount of superabsorbent polymer ("SAP") particles. The absorbent material comprises at least 80%, in particular at least 85%, 90%, 95% and up to 100%, of superabsorbent polymer particles by weight of the absorbent material. The absorbent material may in particular comprise no or only small amount of cellulose fibers, such as less than 20%, in particular less than 10%, 5% or even 0% of cellulose fibers by weight of the absorbent material. The absorbent material may thus advantageously consist or consist essentially of superabsorbent polymer particles.

The terms "superabsorbent polymer particles" refer to absorbent materials in particulate forms which may be crosslinked polymeric materials that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or 24 to 30 g/g. The SAP useful in the present invention includes a variety of water-insoluble, but water-swellable polymers capable of absorbing large quantities of fluids.

The superabsorbent polymers are in particulate form so as to be flowable in the dry state and thus easily deposited on the substrate. Typical particulate absorbent polymer materials are made of poly(meth)acrylic acid polymers. However, starch-based particulate absorbent polymer materials may also be used, as well polyacrylamide copolymer, ethylene maleic anhydride copolymer, crosslinked carboxymethylcellulose, polyvinyl alcohol copolymers, crosslinked polyethylene oxide, and starch grafted copolymer of polyacrylonitrile. The superabsorbent polymer may be polyacrylates and polyacrylic acid polymers that are internally and/or surface crosslinked. Suitable materials are described in WO 07/047598, WO 07/046052, WO 2009/155265 and WO 2009/155264. In some embodiments, suitable superabsorbent polymer particles may be obtained by current state of the art production processes as is more particularly as described in WO 2006/083584. The superabsorbent polymers are preferably internally crosslinked, i.e. the polymerization is carried out in the presence of compounds having two or more polymerizable groups which can be free-radically copolymerized into the polymer network. In some embodiments, the SAP are formed from polyacrylic acid polymers/polyacrylate polymers, for example having a neutralization degree of from 60% to 90%, or about 75%, having for example sodium counter ions.

The SAP particles may be relatively small (under 1 mm in their longest dimension) in their dry state and may be roughly circular in shape, but granules, fibers, flakes, spheres, powders, platelets and other shapes and forms are also known to persons skilled in the art. Typically, the SAP is in the form of spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 to 850 µm, preferably from 100 to 710 µm, more preferably from 150 to 650 µm, as measured according to EDANA method WSP 220.2-05. SAP having a relatively low particle size help to increase the surface area of the absorbent material which is in contact with liquid exudates and therefore support fast absorption of liquid exudates.

The absorbent core will typically comprise only one type of SAP, but it is not excluded that a blend of SAPs may be used. The fluid permeability of a superabsorbent polymer can be quantified using its Urine Permeability Measurement (UPM) value, as measured in the test disclosed European patent application number EP 12174117.7. The UPM of the SAP may for example be of at least $10\times10^{-7}$ cm$^3$·sec/g, or at least $30\times10^{-7}$ cm$^3$·sec/g, or at least $50\times10^{-7}$ cm$^3$·sec/g, or more, e.g. at least 80 or $100\times10^{-7}$ cm$^3$·sec/g. The flow characteristics can also be adjusted by varying the quantity and distribution of the SAP used in the second absorbent layer.

The absorbent material is deposited on the substrate 16 in a pattern having absorbent material land areas 75 separated by absorbent material-free junction areas 76. Examples of such a pattern have been described in details for example in WO2008/155699. In the example represented in FIG. 1, the absorbent material land areas 75 are of generally rectangular shape in the plane of the substrate with the longest side orientated in the transversal direction. The structure may comprise for example between 5 and 30 of these generally rectangular land areas 75. These land areas may have for example a width ranging from 4 to 20 mm, in particular 10 mm, as measured in the longitudinal direction (y). The land areas 75 may be of uniform width but they may have different width, in particular towards the center or crotch section of the absorbent structure to form so called "dog bone" or "hour-glass" shape, which shows a tapering along its width at least in the crotch zone of the structure. The junction areas 76 between the land areas 75 may have a width exemplarily ranging from 0.5 to 10 mm, for example 1 to 5 mm. Of course other patterns of deposition of the absorbent material are possible, thus for example as an array of circular or ovoid land areas, or combination of rectangular land areas with circular or ovoid land areas.

In many applications, the liquid discharge occurs predominantly in one area of the core. For diapers, the liquid may predominantly be released towards the central zone 37 (also called crotch area) of the core and to a lesser extent the front 38 of the core. Relatively less liquid may be released towards the back 36 of the core. Thus it is may be beneficial to profile the amount of absorbent material along the longitudinal direction of the absorbent structure so that more absorbent material is present in the areas where the liquid is more likely to insult the core.

As used herein, the absorbent material deposition area 73 is defined as the smallest area in the plane of the substrate whose periphery encompasses the land areas 75 and the junction areas 76 between the land areas. In order to quantify the amount of profiling, the absorbent material deposition area 73 can be virtually divided in eight deposition zones (Z1-Z8) of equal length as measured along the longitudinal direction of the structure. The zones may be of equal width and equal surface if the absorbent material deposition area 73 is rectangular, but it is not excluded that the zones may have varying width for example in the case of shaped absorbent material deposition area, e.g. having a tapering towards the crotch region of the core.

The absorbent structures of the invention are profiled along the longitudinal direction of the structure so that at least one of the eight deposition zones (Z1, Z2, Z7, Z8) is a zone of lower amount of absorbent material. A zone of lower absorbent material amount is defined herein as a zone having an amount of absorbent material that is at least 20% by weight lower than the average amount of absorbent material in the whole absorbent material deposition area 73 (that is the eight zones together). These zones of lower absorbent material amount may be present towards the front and/or back of the deposition area 73 as represented by zones Z1, Z2, Z7, Z8 in FIG. 1, but it is not excluded that one or more zones of lower absorbent material amount may also be present towards the center of the deposition area. The zone of lower absorbent material amount may further have an amount of absorbent material that is at least 40%, or 50%, or 60%, in particular ranging from 20% to 80%, by weight lower than the average amount of absorbent material in the whole absorbent material deposition area 73.

The zones of lower absorbent material amount require less immobilization of the SAP than the other zones, so that less auxiliary glue is required in these zones. In particular, the auxiliary glue may be absent in at least one, and advantageously all, of the zones of lower absorbent material. The auxiliary glue may also be present but in an amount of at least 50% by weight lower than the average amount of auxiliary glue in the eight absorbent material deposition zone. The invention thus provide for the overall reduction of adhesive material usage by saving the auxiliary glue in the zones where it is less needed. The fibrous thermoplastic adhesive layer 74 may still be present in these zones of lower amount as shown in FIG. 1, to provide the required SAP immobilization, but it is not excluded that even the fibrous thermoplastic layer may be excluded from these zones.

On the other hand, some of the absorbent material deposition zones may also have relatively higher amount of SAP deposited. Thus for example the deposition zones Z4, Z5, Z6 towards the center of the deposition area 73 maybe zones of higher absorbent material amount. More generally, the absorbent structure may have at least one zone of deposition having an amount of absorbent material that is at least 20% higher than the average amount of absorbent material in the absorbent material deposition area 73. The auxiliary glue 72 may be advantageously present in at least one of these zones of higher absorbent material amount, as these zones will be advantageously stabilized by the auxiliary glue.

The amount of absorbent material in each zone may be normally directly calculated from the formula card of the absorbent core considered. Typically modern SAP application process allows for a reliable and reproducible application of the SAP. In case of an absorbent core made by a third party where the formula card of the core is not available, the amount of absorbent material in each zones may be measured analytically using known methods. For example once the absorbent material deposition area and its eight zones are determined (visually or by X-ray), each of the eight zones may be cut from the absorbent core and each cut can then be analyzed for the amount of SAP individually by any standard methods such as titration or gravimetric analysis. The same applies to determine the auxiliary glue application pattern. UV light may be useful to determine where the glue has been applied.

The absorbent material may be deposited in the absorbent material deposition area 73 using known techniques, which may allow relatively precise deposition of SAP particles at relatively high speed. In particular the SAP printing technology as disclosed for example in US2006/24433 (Blessing), US2008/0312617 and US2010/0051166A1 (both to Hundorf et al.) may be used. This technique uses a printing roll to deposit SAP particles onto a substrate disposed on a grid of a support which may include a plurality of cross bars extending substantially parallel to and spaced from one another so as to form channels extending between the cross-bars. In addition to be profiled in the longitudinal direction, the absorbent material may also be deposited at different basis weight in the transversal direction, so that, for example there is higher amount of absorbent material towards the center longitudinal axis of the structure relative to its longitudinal sides.

In general, the auxiliary glue application area 71 may be smaller than the absorbent material deposition area 73. In particular, the surface of the auxiliary glue application area 71 may be no greater than 80%, optionally no greater than 70%, or no greater than 60%, or no greater than 50%, than the surface of the absorbent material deposition area 73, the surface being measured in the plane of the structure. The surface of the auxiliary glue application area 71 may be in particular in the range of from 20% to 80% of the surface of the absorbent material deposition area 73.

Other Examples of Shape of the Application Area 71 and Deposition Area 73

FIG. 1 shows an example where the auxiliary glue application area 71 and absorbent material deposition area 73 are both rectangular, have about the same width and wherein the application area 71 is longitudinally shorter than the deposition area 73 and does not extend to any of the front or back ends of the absorbent material deposition area. FIGS. 8 to 11 show alternative examples of geometries for these areas, which will addressed below. The auxiliary glue and the absorbent material may be applied in these areas according to any of the possibilities described above. The individual features of these further geometry examples may be combined with any other features of other examples or of the general section of this description unless otherwise indicated.

Figure 8:
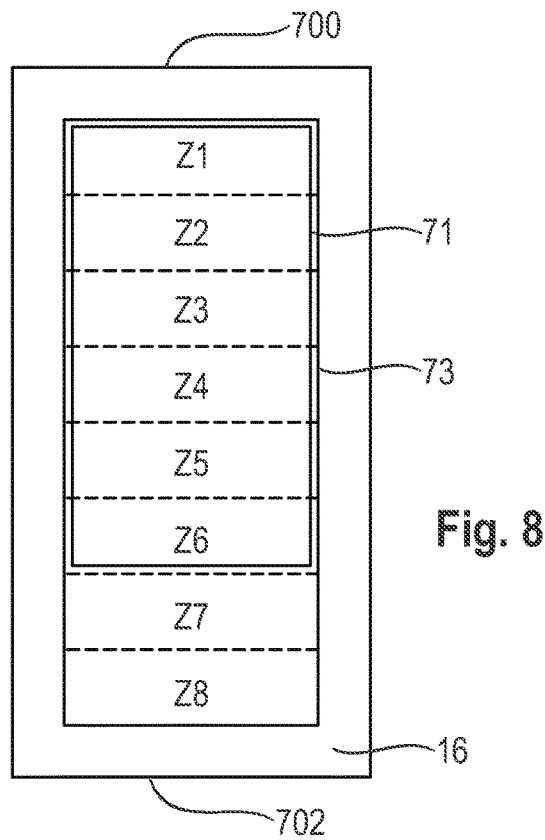
FIGS. 8-11 schematically show alternative outlines for the auxiliary glue application area and absorbent material deposition area.

FIG. 8 shows for example an auxiliary glue application area 71 which extends from the front end of the absorbent material deposition area 73 and wherein both areas have about the same width (the borders of the area 71 have been shown slightly inwards of those of the area 73 for better understanding). This may be advantageous for structures having a relatively high amount of AGM towards the front of the structure, where more auxiliary glue may be needed. As in FIG. 1, the auxiliary glue may be absent from at least one zone Z7, Z8 towards the back of the absorbent material deposition area 73.

Figure 9:
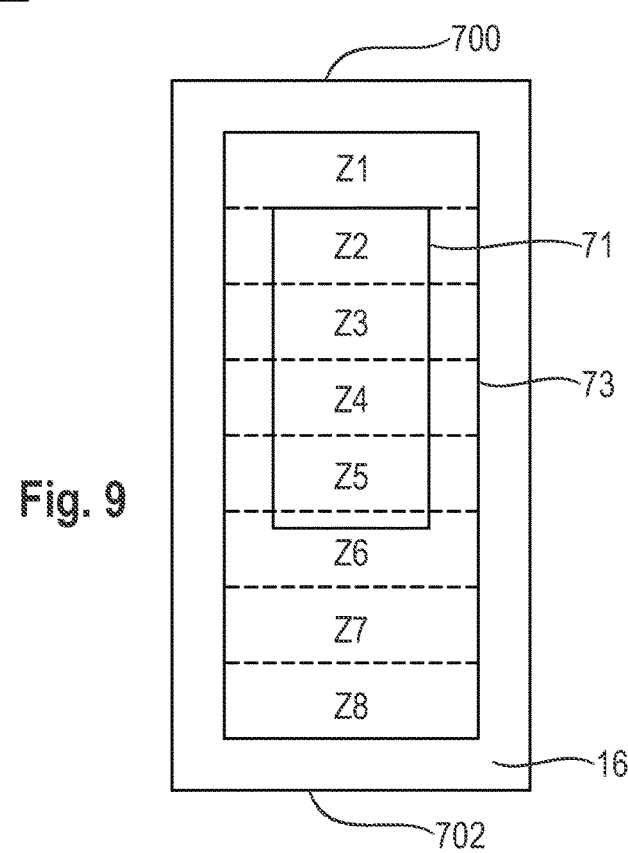

FIG. 9 shows another example, where the auxiliary glue deposition area 71 is less wide than the absorbent material deposition area 73. This embodiment may be for example interesting when the absorbent material is applied in a profiled way in the transversal direction with a higher basis weight towards the longitudinal centerline of the structure. In this way the auxiliary glue is present where the absorbent material is in higher amount.

Figure 10:
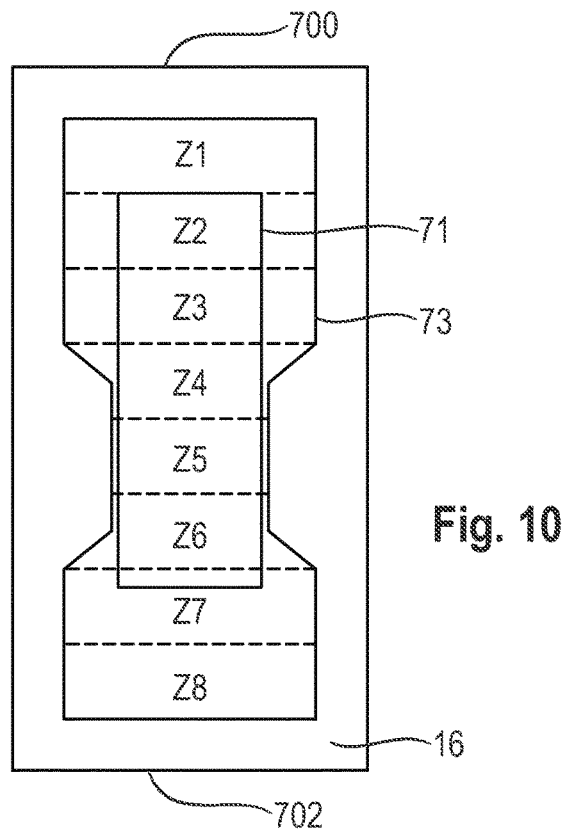

FIG. 10 shows another example where the absorbent material deposition area 73 is shaped in the plane of structure so as to show a tapering in the central zone of the structure. This may be advantageous in order to provide a shaped core which may provide better fit of the absorbent article in the crotch section, for example for absorbent diaper application.

Figure 11:
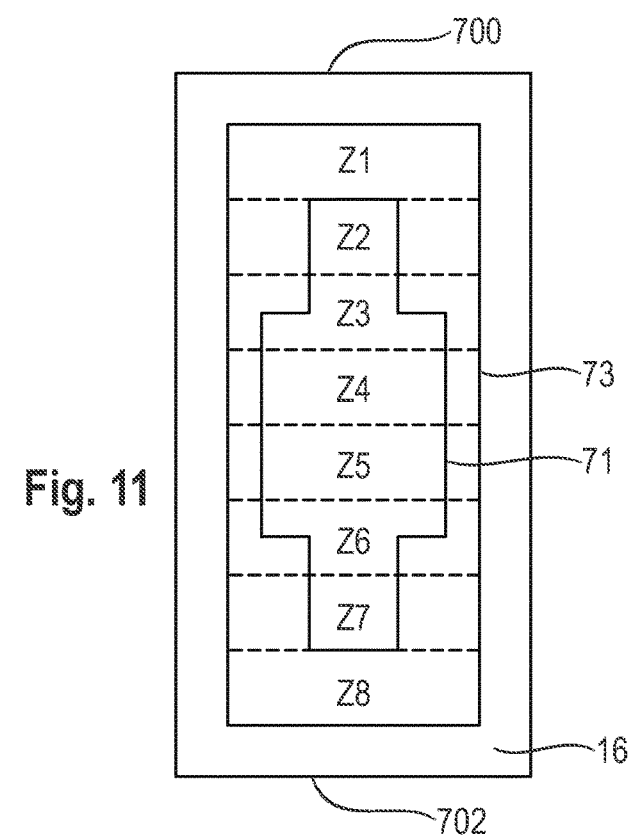

FIG. 11 shows another example where the auxiliary glue application area is not rectangular but has a central body with two adjoined side wings. These side wings may be larger than the central body. The wings as shown do not extend to the transversal edges of the deposition area 73 but they may also extend to these edges if desired. These sections of different lengths may for example be easily obtained using a slot coating process and tuning the slot nozzles to apply the hot-melt adhesive on a shorter distance on the transversal sides of the application area 71 compared to the lateral center of the application area 71.

Fibrous Thermoplastic Adhesive Layer 74

The absorbent structure comprises a fibrous thermoplastic adhesive layer 74 which covers at least some, and advantageously all, of the land areas 75 and the absorbent material-free junction areas 76 in-between in order to provide further immobilization of at least some, advantageously all, of the absorbent material on the substrate and then within the absorbent core. The fibrous thermoplastic adhesive may be sprayed over the absorbent material so as to cover the absorbent material land areas and junction areas. This imparts an essentially three-dimensional structure to the fibrous layer of thermoplastic adhesive 74, which in itself is essentially a two-dimensional structure of relatively small thickness, as compared to the dimensions in length and width directions. Thereby, the fibrous thermoplastic adhesive may provide cavities to cover the absorbent material in the land areas, and thereby immobilizes the absorbent material, which as already indicated may be 100% SAP particles.

The adhesive polymers useful to form the fibrous layer 74 are for example described in WO2008/155699 starting on page 19, last paragraph. The thermoplastic adhesive may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hot-melt adhesive comprising at least one thermoplastic polymer in combination with other thermoplastic diluents such as tackifying resins, plasticizers and additives such as antioxidants.

The thermoplastic polymer may typically have a molecular weight (Mw) of more than 10,000 and a glass transition temperature (Tg) usually below room temperature or $-6°$ C.$<$Tg$<16°$ C. Typical concentrations of the polymer in a hot-melt are in the range of about 20 to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hot-melt are in the range of about 30 to about 60%, and the plasticizer has a low Mw of typically less than 1,000 and a Tg below room temperature, with a typical concentration of about 0 to about 15%.

The thermoplastic adhesive of the thermoplastic material layer 74, 74' is applied as fibers. The fibers may exemplarily have an average thickness of about 1 to about 50 micrometers or about 1 to about 35 micrometers and an average length of about 5 mm to about 50 mm or about 5 mm to about 30 mm. The thermoplastic adhesive of the thermoplastic material layer 74, 74' may be applied with a basis weight in the range from 2 gsm to 20 gsm, optionally from 2 gsm to 10 gsm, for example 3 or 4 gsm.

The thermoplastic adhesive used for the thermoplastic material layer 74, 74' may have elastomeric properties, such that a fibrous layer formed on the SAP layer is able to be stretched as the SAP swells. Exemplary elastomeric, hot-melt adhesives include thermoplastic elastomers such as ethylene vinyl acetates, polyurethanes, polyolefin blends of a hard component (generally a crystalline polyolefin such as polypropylene or polyethylene) and a soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers; mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 (Korpman). A commercial example of elastomeric hot-melt adhesive suitable is Fuller NW1151.

The thermoplastic adhesive used for the auxiliary glue 72 may or may not comprise any of the adhesive types described above in relation to the thermoplastic fibrous adhesive layer 74. The auxiliary glue 72 may be the same or different as the adhesive of the fibrous thermoplastic adhesive 74. The adhesives are preferably selected for their compatibility, so that the auxiliary glue can also serve to improve the adhesion of the fibrous adhesive layer 74 to the substrate 16. Using the same basic adhesive formulation for both layers may be advantageous in terms of adherence performance but it may also be preferred to use a cheaper adhesive for the auxiliary glue as elastomeric properties may not be advantageous for the auxiliary glue layer.

Absorbent Core 28

Although the absorbent structure 70 of the invention may be used directly in an absorbent article without further assembly, the absorbent structure may typically be assembled with other components to form an absorbent core before being introduced in an absorbent article. Such an absorbent core 28 comprises a second substrate 16' placed in face to face relationship with the first substrate 16 to form a core wrap which defines the external surfaces of the core. The two substrates may thus form a core wrap enclosing the absorbent material of the core.

The absorbent core 28 may typically be generally substantially flat in a plane being the same as the plane formed by the longitudinal direction x and transversal direction y of the substrate 16. The absorbent core will typically be thin, being thus understood that the FIGS. 3 to 7 are schematic and shows an exaggeration of the inner layer of the structure/core in the vertical direction. In particular, the maximum caliper of the core (before use) as measured according to the Core Caliper Test as described herein may be from 0.25 mm to 5.0 mm, in particular from 0.5 mm to 4.0 mm. The full length L' of the core may be the same length as the length of any or both of the substrates, and can be measured from the core's front edge 280 to its back edge 282 along its central longitudinal axis. It may for example be at least 320 mm, for example from 320 mm to 600 mm, for typical diaper applications, but may be shorter for smaller articles.

The substrates may be comprise at least one, typically two, transversal end seals 280, 282 and at least one, typically two, longitudinal side seals 284, 286, wherein the seals can be continuous or discontinuous along their lengths. Typically the absorbent material will be advantageously distributed in somewhat higher amount towards the front edge 280 than towards the back edge as more absorbency is required at the front of the core (assuming the front of core will be placed towards the front of the article). Typically the front and back edges of the core are shorter than the longitudinally extending side edges of the core. The absorbent core 28 may also comprise a top side and a bottom side, which are substantially concomitant with the external surfaces of the first and second substrate or vice versa.

Figure 4:
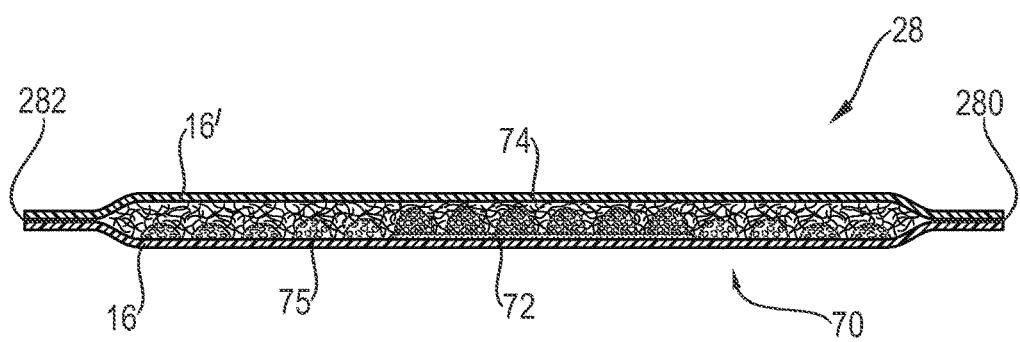
FIG. 4 is a longitudinal cross-section of an absorbent core comprising the absorbent structure of FIGS. 1-3 and a second substrate.

FIG. 4 shows a cross-section of an absorbent core 28 comprising an absorbent structure 70 assembled directly with a second substrate 16'. The second substrate may be made of the same material as the substrate 16. Typically, the side of the core intended to be placed towards the wearer in the finished absorbent article will be hydrophillically treated and the side of the core placed towards the backsheet may be inherently hydrophobic or hydrophobically treated, so that the liquid can more easily penetrate into and remain inside the core.

Figure 5:
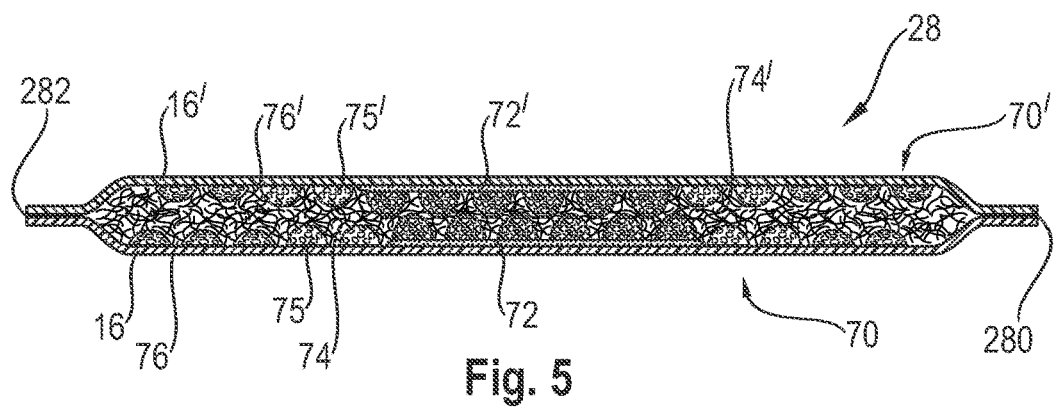
FIG. 5 is a longitudinal cross-section of an absorbent core comprising the absorbent structure of FIGS. 1-3 and a second absorbent structure comprising a second auxiliary glue.
Figure 6:
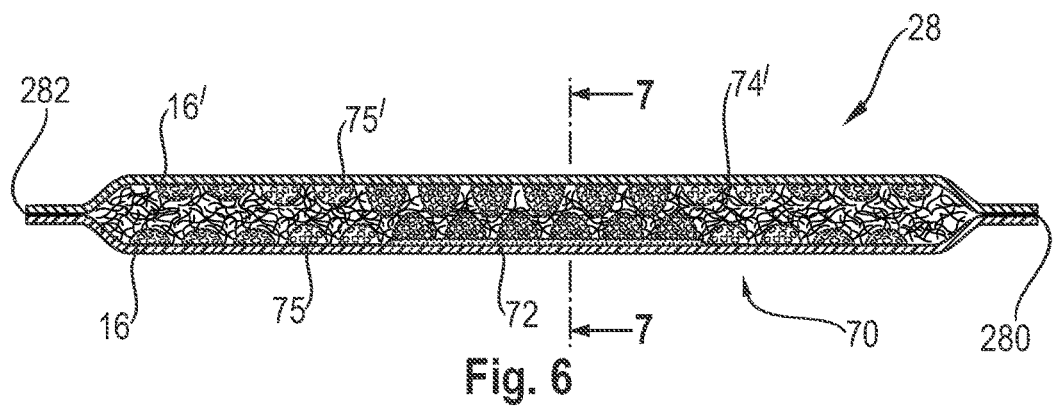
FIG. 6 is a longitudinal cross-section of an absorbent core comprising the absorbent structure of FIGS. 1-3 and a second absorbent structure that does not comprise an auxiliary glue.

It may be advantageous that the absorbent core comprises a second absorbent structure 70' comprising a second absorbent material, as exemplarily represented in FIGS. 5 and 6. The second absorbent structure may or may not be a structure according to the invention, in particular it may or may not comprise a secondary auxiliary glue 72'. The second absorbent material may also be deposited on the second substrate 16' in a pattern of absorbent material land areas 75' separated by absorbent material-free junction areas 76'. When the first and second absorbent structures are combined together to form the core, the respective patterns of land areas and junction areas of the absorbent structures may be advantageously placed offset from each other so that the absorbent material placed between the substrates form an absorbent particulate polymer area layer 8 which is substantially continuous. Such a dual composite structure of matching land areas and junction areas is for example disclosed in WO2008/155699 (Hundorf).

The second absorbent structure 70' may thus comprise a second substrate 16', a second absorbent material comprising from 80% to 100% by weight of superabsorbent particles and deposited on the substrate in a pattern of absorbent material land areas 75' separated by absorbent material-free junction areas 76', a second fibrous thermoplastic adhesive layer 74' arranged to cover at least some of the land areas 75' and the absorbent material-free junction areas 76' to thereby immobilize at least some of the second absorbent material on the second substrate, and a optionally a second auxiliary glue 72' applied directly over the second substrate. However, other patterns are possible including so-called islands-in-the-sea arrangements with either the absorbent material areas or the absorbent material-free areas defining the islands, as described in US2008/0312622 A1 (Hundorf), for example. The second absorbent material could, alternatively, take other forms, such as a mixed layer of cellulose-based absorbent material and superabsorbent material.

If present, the second auxiliary glue 72' may be applied across a limited length of the second of substrate as shown on FIG. 5. The second absorbent structure may then also be an absorbent structure according to the first aspect of the invention, wherein the second absorbent material deposition area can be notionally divided in eight deposition zones of equal length along its longitudinal direction; and having at least one deposition zones of lower absorbent material amount having an amount of absorbent material that is at least 20% by weight lower than the average amount of absorbent material in the whole second absorbent material deposition area and wherein the auxiliary glue 72' is absent or in reduced amount in at least one of these deposition zones of lower absorbent material amount. The second absorbent material deposition area is defined similarly as the first absorbent material deposition area and is the smallest area in the plane of the second substrate 16' whose periphery encompasses the land areas 75' and the junction areas 76' between the land areas.

The second absorbent structure may alternatively also have no auxiliary glue 72' directly applied on the second substrate 16', as exemplarily shown on FIG. 6. This provides further material savings and may represent an appropriate compromise if the first auxiliary glue layer together with the fibrous thermoplastic layers 74, 74' provide enough SAP immobilization.

Figure 7:
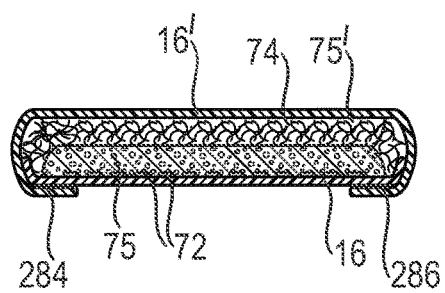
FIG. 7 shows a transversal cross-section of the core of FIG. 6.

FIG. 7 shows a schematic cross-section of the core of FIG. 6. It is to be understood that the fibrous adhesive layer is shown in this view in exaggerated form and that in reality the second substrate 16' would appear in contact with the absorbent material in the land areas 75. In general, the core wrap formed by the substrates 16, 16' may be sealed along its front edge 280 and back edge 282. FIG. 7 further shows typical so-called C-wrap seals 284, 286 along each of the longitudinal side edge of the core, wherein one of the substrate forms a transversally extending flap along each side edge of the core, each flap being folded around an edge of the core and then attached to the external surface of the other substrate on the other side of the core. The C-wrap seal can be typically be formed by providing one of the substrate with a larger width than the second substrate, applying an adhesive along each of the transversal edges of the larger substrate and then folding these two extending flaps over the longitudinal edges of the core and unto the external surface of the other substrate. The adhesive applied provides for a secure seal along the edges of the core that have been C-wrapped, typically the longitudinal edges. The C-wrap seals may typically be glued but other bonding means are not excluded. The front edge seal 280 and back edge seal 282 of the core may be performed by any known means, in a particular in a sandwich wrap configuration as shown on FIG. 5 and FIG. 6 wherein the internal surfaces of the two substrates are bonded to each other on a face to face relationship. The front and back transversal seals may use gluing, e.g. using a series of glue lines longitudinally oriented, or hot crimping. The seals of the core wrap may also be provided by any other conventional means and may be intermittent or continuous.

The absorbent cores and structure of the invention may comprise one or more channels partially oriented in the longitudinal direction, as exemplarily disclosed in WO2012/170778 (Rosati et al., see also WO2012/170779, WO2012/170781 and WO2012/170808. The absorbent core and structures of the invention may also be devoid of such channels. The channels may be formed in various ways. For example, the channels may be formed by openings within the absorbent material layer inside the core wrap. The channels may be substantially or completely free of absorbent material, in particular SAP. In addition or alternatively, the channels may be formed by continuously or discontinuously bonding the first substrate to the second substrate through the absorbent material layer in areas substantially free of absorbent material. The substrates in these channels may be continuously or discontinuously bonded to each other. Other layers between the topsheet 24 and the absorbent core 28 may or may not also comprise channels, which may or may not correspond to the channels of the absorbent core 28. The absorbent core may also not comprise any of such channels.

The total amount of SAP present in the absorbent core may also vary according to expected usage. Diapers for newborns may require less SAP than infant or adult incontinence diapers. The amount of SAP in the core may be for example comprised from about 5 to 60 g, in particular from 10 to 25 g. The average SAP basis weight within the absorbent material layer 8 within the core may be for example of at least 50, 100, 200, 300, 400, 500 or more g/m$^2$. The absorbent core may further also advantageously achieve an SAP loss of no more than about 70%, 60%, 50%, 40%, 30%, 20%, or 10% according to the Wet Immobilization Test described in WO 2010/0051166 A1.

General Description of the Absorbent Article 20

Figure 12:
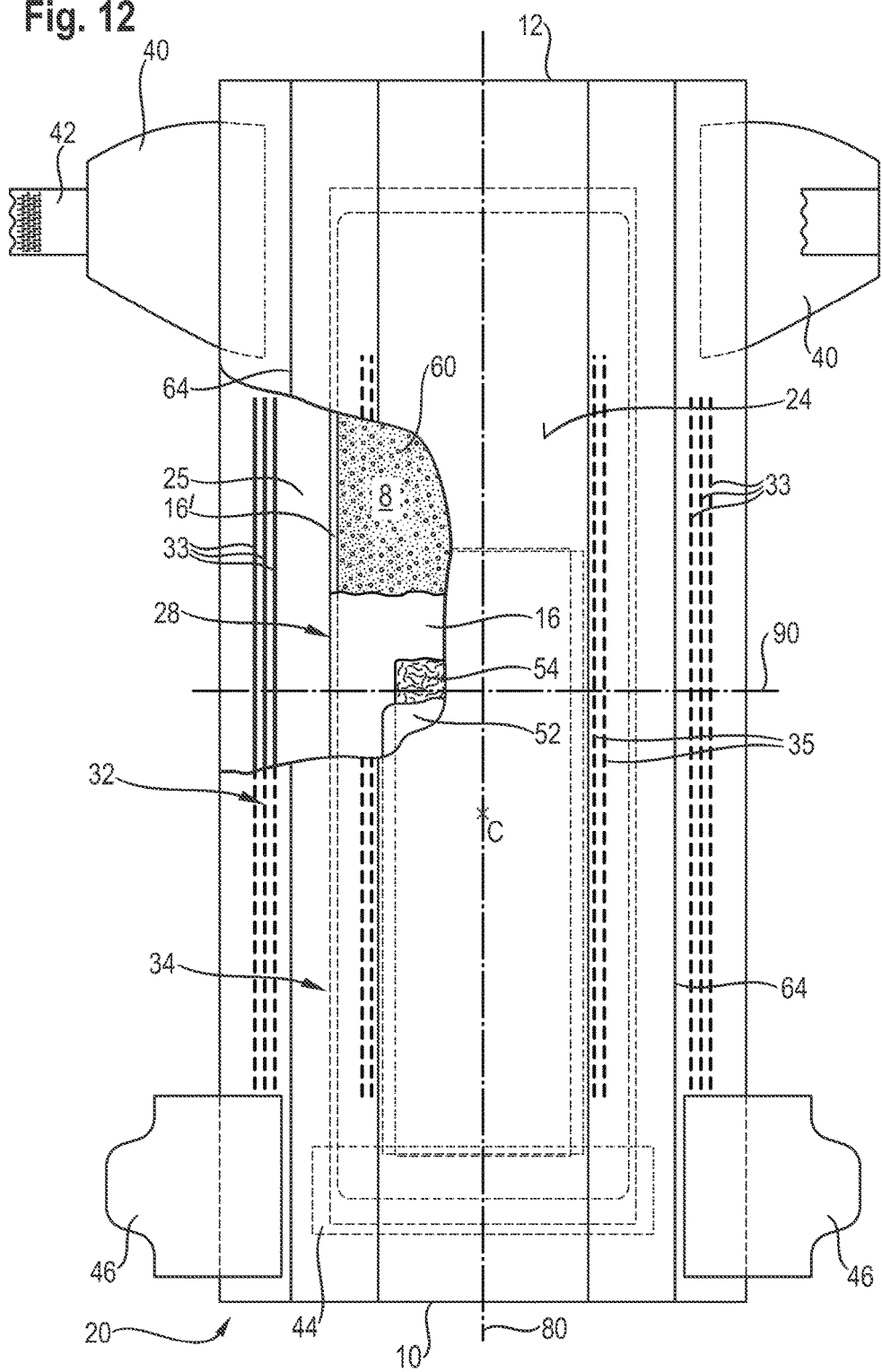
FIG. 12 shows an exemplary absorbent article in the form of a diaper comprising an absorbent core of the invention.

The absorbent core comprising the absorbent structure of the invention or the absorbent structure itself will typically be used in an absorbent article. An exemplary absorbent article in the form of an infant diaper 20 is represented in FIG. 12. FIG. 12 is a top plan view of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles.

The absorbent article 20 comprises a liquid permeable topsheet 24, a liquid impermeable backsheet 25 and an absorbent core 28 positioned between the topsheet 24 and the backsheet 25. The absorbent article may also comprise further typical components such as an acquisition layer 52 and/or a distribution layer 54 (collectively referred to as acquisition-distribution system "ADS"), and elasticized gasketing cuffs 32 present between topsheet and backsheet and upstanding barrier leg cuffs 34, which will be further detailed in the following. FIG. 12 also show other typical taped diaper components such as a fastening system comprising fastening tabs 42 attached towards the back edge 12 of the article and cooperating with a landing zone 44 towards the front edge of the article. The absorbent article may also comprise other typical components, which are not represented in the Figures, such as a back elastic waist feature, a front elastic waist feature, transverse barrier cuffs, a lotion application, etc.

The absorbent article 20 comprises a front edge 10, a back edge 12, and two side edges. The front edge 10 is the edge of the article which is intended to be placed towards the front of the user when worn, and the back edge 12 is the opposite edge. The absorbent article may be notionally divided by a longitudinal axis 80 extending from the front edge to the back edge of the article and dividing the article in two substantially symmetrical halves relative to this axis, when viewing the article from the wearer facing side in a flat out configuration, as exemplarily shown in FIG. 12. If some part of the article is under tension due to elasticized components, the article may be typically flattened using clamps along the periphery of the article and/or a sticky surface, so that the topsheet and backsheet can be pulled taut so as to be substantially flat. Unless otherwise indicated, dimensions and areas disclosed herein apply to the article in this flat-out configuration.

The absorbent article 20 can also be notionally divided by a transversal axis 90 into a front region and a back region of equal length measured on the longitudinal axis, when the article is in such a flat state. This article's transversal axis 90 is perpendicular to the longitudinal axis 80 and placed at half the length of the article. The length of the article can be measured along the longitudinal axis 80 from front edge 10 to back edge 12.

The topsheet 24, the backsheet 25, the absorbent core 28 and the other article components may be assembled in a variety of well-known configurations, in particular by gluing and/or heat embossing. Exemplary diaper assemblies are for example generally described in U.S. Pat. Nos. 3,860,003, 5,221,274, 5,554,145, 5,569,234, 5,580,411, and 6,004,306. The absorbent article is preferably thin. The article may be advantageously thin at the intersection of the longitudinal and transversal axes, for example with a caliper of from 1.0 mm to 8.0 mm, in particular from 1.5 mm to 6.0 mm, as measured using the Absorbent Article Caliper Test described below.

Topsheet 24

The topsheet 24 is the part of the absorbent article 20 that is directly in contact with the wearer's skin. The topsheet 24 can be joined to the backsheet 25, the absorbent core 28 and/or any other layers as is known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). Usually, the topsheet 24 and the backsheet 25 are joined directly to each other in some locations (e.g. on or close to the periphery of the article) and are indirectly joined together in other locations by directly joining them to one or more other elements of the article 20.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 4,629,643. Such formed films are available from The Procter & Gamble Company of Cincinnati, Ohio as "DRI-WEAVE" and from Tredegar Corporation, based in Richmond, Va., as "CLIFF-T".

Any portion of the topsheet may be coated with a lotion as is known in the art. Examples of suitable lotions include those described in U.S. Pat. Nos. 5,607,760, 5,609,587, 5,643,588, 5,968,025 and 6,716,441. The topsheet 24 may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 cm$^2$ and about 50 cm$^2$, in particular between about 15 cm$^2$ and 35 cm$^2$. Examples of apertured topsheet are disclosed in U.S. Pat. No. 6,632,504. WO 2011/163582 also discloses suitable colored topsheet having a basis weight of from 12 to 18 gsm and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet. Typical diaper topsheets have a basis weight of from about 10 to about 28 gsm, in particular between from about 12 to about 18 gsm but other basis weights are possible.

Backsheet 25

The backsheet 25 is generally that portion of the absorbent article 20 which forms the external surface of the article when worn by the user. The backsheet 25 is positioned towards the bottom side of the absorbent core 28 and prevents the exudates absorbed and contained therein from soiling articles such as bed sheets and undergarments. The backsheet 25 is typically impermeable to liquids (e.g. urine). The backsheet 25 may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the article 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in WO 95/16746 (E. I. DuPont), U.S. Pat. No. 5,938,648 (LaVon et al.), U.S. Pat. No. 4,681,793 (Linman et al.), U.S. Pat. No. 5,865,823 (Curro), U.S. Pat. No. 5,571,096 (Dobrin et al.) and U.S. Pat. No. 6,946,585 (London Brown).

The backsheet 25 may be joined to the topsheet 24, the absorbent core 28 or any other element of the diaper 20 by any attachment means known in the art. Suitable attachment means are described above with respect to means for joining the topsheet 24 to other elements of the article 20. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996; and 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Acquisition-Distribution System

The absorbent articles of the invention may comprise an acquisition layer 52, a distribution layer 54, or combination of both (herein collectively referred to as acquisition-distribution system "ADS"). The function of the ADS is typically to quickly acquire the fluid and distribute it to the absorbent core in an efficient manner. The ADS may comprise one, two or more layers, which may form a unitary layer or remain discrete layers which may be attached to each other. In the examples below, the ADS comprises two layers: a distribution layer 54 and an acquisition layer 52 disposed between the absorbent core and the topsheet, but the invention is not restricted to this example.

Typically, the ADS will not comprise SAP as this may slow the acquisition and distribution of the fluid. The prior art discloses many type of acquisition-distribution system, see for example WO 2000/59430 (Daley), WO 95/10996 (Richards), U.S. Pat. No. 5,700,254 (McDowall), WO 02/067809 (Graef). The ADS may, although not necessarily, comprise two layers: a distribution layer 54 and an acquisition layer 52, which will now be exemplified in more detail.

Distribution Layer 54

The function of a distribution layer 54 is to spread the insulting fluid liquid over a larger surface within the article so that the absorbent capacity of the core can be more efficiently used. Typically the distribution layer is made of a nonwoven material based on synthetic or cellulosic fibers and having a relatively low density. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer 54 may also be a material having a water retention value of from 25 to 60, preferably from 30 to 45, measured as indicated in the procedure disclosed in U.S. Pat. No. 5,137,537. The distribution layer 54 may typically have an average basis weight of from 30 to 400 g/m$^2$, in particular from 100 to 300 g/m$^2$.

The distribution layer 54 may for example comprise at least 50% by weight of crosslinked cellulose fibers. The crosslinked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The crosslinked cellulosic fibers provide higher resilience and therefore higher resistance against the compression in the product packaging or in use conditions, e.g. under baby weight.

Exemplary chemically crosslinked cellulosic fibers suitable for a distribution layer are disclosed in U.S. Pat. Nos. 5,549,791, 5,137,537, WO 95/34329 or US 2007/118087. Exemplary crosslinking agents include polycarboxylic acids such as citric acid and/or polyacrylic acids such as acrylic acid and maleic acid copolymers. For example, the crosslinked cellulosic fibers may have between about 0.5 mole % and about 10.0 mole % of a C2-C9 polycarboxylic acid crosslinking agent, calculated on a cellulose anhydroglucose molar basis, reacted with said fibers in an intrafiber ester crosslink bond form. The C2-C9 polycarboxylic acid crosslinking agent may be selected from the group consisting of:

aliphatic and alicyclic C2-C9 polycarboxylic acids having at least three carboxyl groups per molecule; and aliphatic and alicyclic C2-C9 polycarboxylic acids having two carboxyl groups per molecule and having a carbon-carbon double bond located alpha, beta to one or both of the carboxyl groups, wherein one carboxyl group in said C2-C9 polycarboxylic acid crosslinking agent is separated from a second carboxyl group by either two or three carbon atoms. The fibers may have in particular between about 1.5 mole % and about 6.0 mole % crosslinking agent, calculated on a cellulose anhydroglucose molar basis, reacted therewith in the form of intrafiber ester crosslink bonds. The crosslinking agent may be selected from the group consisting of citric acid, 1, 2, 3, 4 butane tetracarboxylic acid, and 1, 2, 3 propane tricarboxylic acid, in particular citric acid.

Polyacrylic acid crosslinking agents may also be selected from polyacrylic acid homopolymers, copolymers of acrylic acid, and mixtures thereof. The fibers may have between 1.0 weight % and 10.0 weight %, preferably between 3 weight % and 7 weight %, of these crosslinking agents, calculated on a dry fiber weight basis, reacted therewith in the form of intra-fiber crosslink bonds. The crosslinking agent may be a polyacrylic acid polymer having a molecular weight of from 500 to 40,000, preferably from 1,000 to 20,000. The polymeric polyacrylic acid crosslinking agent may be a copolymer of acrylic acid and maleic acid, in particular wherein the weight ratio of acrylic acid to maleic acid is from 10:1 to 1:1, preferably from 5:1 to 1.5:1. An effective amount of citric acid may be further mixed with said polymeric polyacrylic acid crosslinking agent.

The distribution layer 54 comprising crosslinked cellulose fibers may comprise other fibers, but this layer may advantageously comprise at least 50%, or 60%, or 70%, or 80%, or 90% or even up to 100%, by weight of the layer, of crosslinked cellulose fibers (including the crosslinking agents). Examples of such mixed layer of crosslinked cellulose fibers may comprise about 70% by weight of chemically crosslinked cellulose fibers, about 10% by weight polyester (PET) fibers, and about 20% by weight untreated pulp fibers. In another example, the layer of crosslinked cellulose fibers may comprise about 70% by weight chemically crosslinked cellulose fibers, about 20% by weight lyocell fibers, and about 10% by weight PET fibers. In another example, the layer may comprise about 68% by weight chemically crosslinked cellulose fibers, about 16% by weight untreated pulp fibers, and about 16% by weight PET fibers. In another example, the layer of crosslinked cellulose fibers may comprise from about 90-100% by weight chemically crosslinked cellulose fibers.

Acquisition Layer 52

The absorbent article 20 may comprise an acquisition layer 52, whose function is to quickly acquire the fluid away from the topsheet so as to provide a good dryness for the wearer. The acquisition layer 52 is typically placed directly under the topsheet. If present, the distribution layer 54 may be at least partially disposed under the acquisition layer 52. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material.

Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US 2003/148684 (Cramer et al.) and US 2005/008839 (Cramer et al.).

The acquisition layer 52 may be stabilized by a latex binder, for example a styrene-butadiene latex binder (SB latex). Processes for obtaining such latices are known, for example, from EP 149880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A further acquisition layer (not shown) may be used in addition to the first acquisition layer 52 described above. For example a tissue layer may be placed between the first acquisition layer 52 and the distribution layer 54. The tissue may have enhanced capillarity distribution properties compared to the acquisition layer 52 described above. The tissue and the first acquisition layer 52 may be of the same size or may be of different size, for example the tissue layer may extend further in the back of the absorbent article than the first acquisition layer 52. An example of a hydrophilic tissue is a 13 to 15 gsm high wet strength tissue made of cellulose fibers from supplier Havix.

Fastening System 42, 44

The absorbent article may include a fastening system. The fastening system can be used to provide transversal tensions about the circumference of the absorbent article to hold the absorbent article on the wearer. This fastening system is not necessary for training pant article since the waist region of these articles is already bonded. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499, 978, 5,507,736, and 5,591,152.

Front and Back Ears 46, 40

The absorbent article may comprise front ears 46 and back ears 40 as is known in the art. The ears can be integral part of the chassis, for example formed from the topsheet and/or backsheet as side panel. Alternatively, as represented in FIG. 12, they may be separate elements attached by gluing and/or heat embossing. The back ears 40 are advantageously stretchable to facilitate the attachment of the tabs 42 on the landing zone 44 and maintain the taped diapers in place around the wearer's waist. The front ears 46 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Barrier Leg Cuffs 34 and Gasketing Cuffs 32

Absorbent articles such as diapers or training pants may typically further comprise components that improve the fit of the article around the legs of the wearer, in particular barrier leg cuffs 34 and gasketing cuffs 32. The barrier leg cuffs 32 may be formed by a piece of material, typically a nonwoven, which is partially bonded to the rest of the article and can be partially raised away and thus stand up from the plane defined by the topsheet, when the article is worn by the user. The barrier leg cuffs 34 can provide improved containment of liquids and other body exudates approximately at the junction of the torso and legs of the wearer. The barrier leg cuffs 34 may extend at least partially between the front edge and the back edge of the absorbent article on opposite sides of the longitudinal axis and may at least be present adjacent to the crotch point (C).

The barrier leg cuffs 34 may be delimited by a proximal edge joined to the rest of the article, typically the topsheet and/or the backsheet, and a free terminal edge intended to contact and form a seal with the wearer's skin. The barrier leg cuffs 34 may be joined at the proximal edge with the chassis of the article by a bond which may be made for example by adhesive bonding, fusion bonding or combination of known bonding means. The bond at the proximal edge may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to this free terminal edge to provide a better seal.

In addition to the barrier leg cuffs 34, the article may comprise gasketing cuffs 32, which are formed in the same plane as the chassis of absorbent article, in particular may be at least partially enclosed between the topsheet and the backsheet, and may be placed transversally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the back side of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is not represented in the Figures, for clarity and readability. Bonding between the layers of the article should be considered to be present unless specifically excluded. Adhesives may be typically used to improve the adhesion of the different layers, for example between the backsheet and the core wrap. The adhesives used may be any standard hot-melt glue as known in the art.

If an acquisition layer 52 is present, it may be advantageous that this acquisition layer is larger than or least as large as the distribution layer 54 in the longitudinal and/or transversal dimension. Thus the distribution layer 54 can be deposited on the acquisition layer 52. This simplifies handling, in particular if the acquisition layer is a nonwoven which can be unrolled from a roll of stock material. The distribution layer may also be deposited directly on the absorbent core's upper side of the core wrap or another layer of the article. Also, an acquisition layer 52 larger than the distribution layer allows one to directly adhere the acquisition layer to the storage core (at the larger areas). This can provide increased article integrity and better liquid communication.

The absorbent core and in particular its absorbent material layer(s) may advantageously be at least as large and long and advantageously at least partially larger and/or longer than any of the layer in the acquisition-distribution system ("ADS"). This is because the absorbent material in the absorbent core 28 can usually more effectively retain fluid and provide dryness benefits across a larger area than the ADS. The absorbent article may have rectangular absorbent material deposition area 8 and a non-rectangular (shaped) ADS. The absorbent article may also have a rectangular (non-shaped) ADS and a rectangular layer of absorbent material 8.

Method of Making

The absorbent article of the invention may be made by any conventional methods known in the art. In particular the articles may be hand-made or industrially produced at high speed on a modern converting line. The absorbent structure and absorbent core of the invention can in particular by adapting the method generally disclosed for making absorbent layers disclosed in WO2008/155699 with some adaptations. Such a method is schematically disclosed in FIG. 13.

Figure 13:
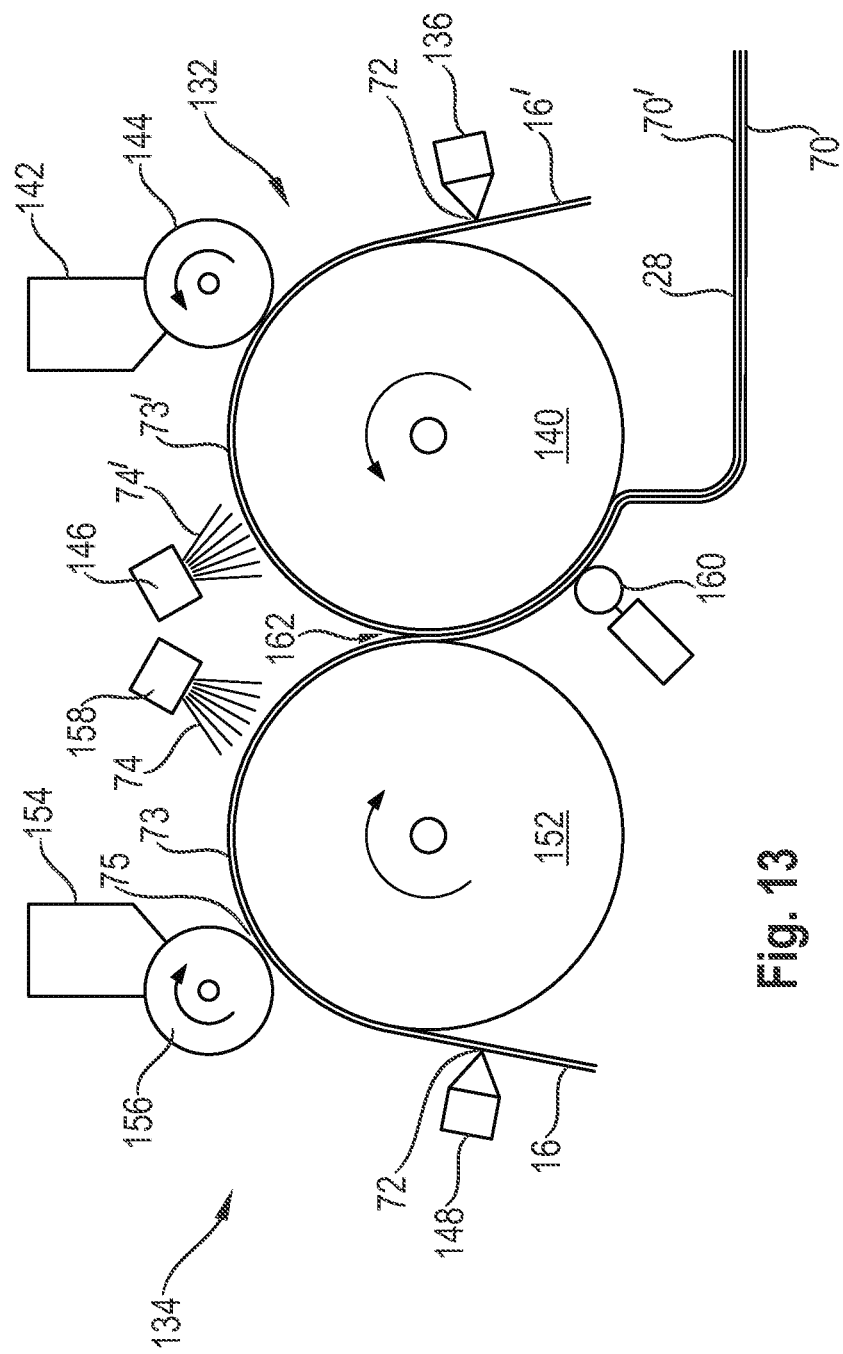
FIG. 13 shows a schematic apparatus for making an absorbent structure and core of the invention. It should be understood that cross-section views have been expanded in the vertical direction to better show the arrangement of the different layers comprised by the structures and cores. The structures and cores thus appear much thicker in these Figures than in reality.

A first printing unit 134 for making an absorbent structure in accordance with the first aspect of this invention is illustrated on the left side of FIG. 13. The first printing unit 134 comprise an auxiliary glue applicator 148 for applying the auxiliary glue 72 to the substrate 16, a first rotatable support roll 152 for receiving the first substrate 16, a first hopper 154 for holding and dispensing the absorbent particulate polymer material, a first printing roll 156 for depositing the absorbent particulate polymer material land areas 75 from the hopper 154 to a deposition area 73 on the substrate 16, and a first thermoplastic adhesive material applicator 158 for applying the fibrous thermoplastic adhesive material 74. The auxiliary glue applicator 148 may be a nozzle system which can provide a relatively thin but wide curtain of thermoplastic adhesive material as suggested in WO2008/155699, but may also alternatively and advantageously comprise a slot coater for applying simultaneously several slots of auxiliary glue 72 longitudinally along the width of the substrate. The auxiliary glue applicator may be fitted with a manifold which intermittently stops the delivery of the auxiliary glue so that there the auxiliary layer is not applied or applied at a reduced amount in the area of the substrate corresponding to the zones of lower absorbent material amount. The SAP printing roll 156 and fibrous layer adhesive applicator 158 may be as further detailed in WO2008/155699.

The absorbent structure 70 obtained by the printing unit 134 may be directly put in face to face relation with a second substrate 16', or may be combined with a second absorbent structure 70', to form an absorbent core. This second absorbent structure 70' may then be formed on the second printing unit 132 as shown on the right side of FIG. 13, which may be generally identical to the first printing unit 134. The second printing unit 132 may comprise a second auxiliary glue applicator 136 which may be a slot coater for applying an auxiliary glue to the substrate 16', a second rotatable support roll 140 for receiving the substrate 16', a second hopper 142 for holding absorbent particulate polymer material, a second printing roll 144 for transferring the absorbent particulate polymer material to the substrate 16', and a thermoplastic adhesive material applicator 146 for applying the thermoplastic fibrous adhesive material 74' to the substrate 16' and the absorbent particulate polymer land areas 75' thereon.

The absorbent structures may for example be combined by applying pressure in the nip between the two support rolls 140, 152. The longitudinal side seals 284, 286 may be formed for example as a C-wrap in the seal forming guide roller 160. The absorbent cores 28 can then be individualized by forming the front and back end seals and cutting the web of the core material at the required interval. The continuous flow of absorbent cores can then be integrated into a converting process for making an absorbent article.

Test Procedures

The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced, if available, on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2-05.

Dry Absorbent Core Caliper Test

This test may be used to measure the caliper of the absorbent core (before use i.e. without fluid loading) in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The core is conditioned at least 24 hours as indicated above.

Measurement procedure: The core is laid flat with the top side, i.e. the side intended to be placed towards the wearer in the finished article facing up. The point of measurement (e.g. the crotch point C) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as for the Dry Absorbent Core Caliper Test with the difference that the caliper of the finished absorbent article is measured instead of the caliper of the core. The point of measurement may be the intersection of the longitudinal axis 80 and transversal axis 90 of the absorbent article, or any other points of the article. If the absorbent articles are provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles Care is taken to avoid touching and/or compressing the area of measurement.

Example

An exemplary absorbent structure according to the first aspect of the invention and roughly corresponding to the schematic view shown in FIG. 1 can be made as follows. The substrate may be e.g. a 10 gsm SMS nonwoven substrate 390 mm long and 130 mm wide. The auxiliary glue (e.g. Fuller hot-melt adhesive 1286 or 1358) can be applied by slot coating in a pattern of 55 slots 1 mm wide with a distance of 1 mm between the slots over a width of about 110 mm. The slots can start at a distance of 105 mm from the front edge of the substrate and extend up to a distance of 140 mm from the back edge of the substrate for a total length 145 mm. The total amount of auxiliary glue on the substrate may be e.g. 0.080 g (80 mg). It is also alternatively possible to apply the auxiliary glue to a shorter width, for example 41 slots 1 mm wide with a separation distance of 1 mm for a width of about 80 mm for the auxiliary glue application area. The application area may be centered on the longitudinal centerline of the substrate.

A superabsorbent polymer in particulate form can be applied on the substrate in rectangular land areas oriented in the transversal direction (x) of the substrate as shown on FIG. 1, each area being about 10 mm wide and 110 mm long. The first land area may start at a distance of 15 mm from the front edge of the substrate. The junction area that separates each land area may be about 1-2 mm long. The last land area may be placed at a distance of 15 mm from the back edge of the substrate, thus providing the substrate with about thirty SAP land areas. The amount of SAP in each land areas may vary so as to provide zones of lower amount and zones of higher amount of absorbent material. The SAP deposition area is notionally divided in 8 zones as illustrated in FIGS. 1 and 2 each zone being in this example 45 mm long and comprising about four SAP land areas. The total amount of SAP in the structure was about 6.75 g, thus an average amount of SAP of 0.844 g (6.75/8) per zone across the whole SAP deposition area. The distribution of SAP for each zone may thus be as follows:

|  | Z1 | Z2 | Z3 | Z4 | Z5 | Z6 | Z7 | Z8 |
|---|---|---|---|---|---|---|---|---|
| Amount of SAP (g) | 0.87 | 0.97 | 1.18 | 1.26 | 1.05 | 0.71 | 0.42 | 0.29 |
| Relative difference (%) | +3.1 | +14.9 | +39.8 | +49.3 | +24.4 | −15.9 | −50.2 | −65.6 |

The relative difference in percent is the actual amount of SAP in the zone minus the average amount in the 8 zones, this being divided by the average amount and multiplied by 100 (in this example=(x−0.844)/0.844*100), where x is the amount of SAP in the zone considered and 0.844 g the average amount.

Zone 7 and zone 8 have amount of absorbent material which are at least 20% by weight lower than the average amount (minus 50.2% and minus 65.6% respectively) and are thus zones of lower amount of absorbent material as defined herein. Zones 3, 4 and 5 are zones of higher amount of absorbent material, having more than 20% by weight of absorbent material relative to the average amount.

The total amount of auxiliary glue in the structure may be 80 mg thus an arithmetic average of 10 mg (80/8) for each zone. The actual repartition in the zones may be as follows, with relative differences being calculated by taking the actual amount minus the average amount and diving the result by the average amount (=(y−10)/10*100), where y is the actual amount:

|  | Z1 | Z2 | Z3 | Z4 | Z5 | Z6 | Z7 | Z8 |
|---|---|---|---|---|---|---|---|---|
| Amount of auxiliary glue (mg) | 0 | 0 | 24.8 | 24.8 | 24.8 | 5.5 | 0 | 0 |
| Relative difference (%) | Absent | Absent | 148% | 148% | 148% | −45% | Absent | Absent |

The auxiliary glue application area is present in absorbent material deposition zones 3, 4, 5 and 6 and absent in zones 1, 2, 7 and 8. Zone Z6 comprises a relatively low amount of auxiliary glue compared to the zones Z3, Z4, Z5. In this example the zones of lower amount of absorbent material (Z7, Z8) do not have auxiliary glue applied thereon, while the zones of higher absorbent material amount have auxiliary glue applied (Z3, Z4, Z5) thereon. As an alternative, it is also possible to also apply the auxiliary glue in the first two zones Z1 and Z2 and also in the rest of Z6 in addition to zones Z3-Z6 as described above, as these zones Z1 and Z2, while not zones of higher amount of SAP, are not zones of lower amount of SAP. Keeping a total amount of 80 mg auxiliary glue for the whole of the absorbent structure, the repartition of the auxiliary glue in the zones is as follow:

|  | Z1 | Z2 | Z3 | Z4 | Z5 | Z6 | Z7 | Z8 |
|---|---|---|---|---|---|---|---|---|
| Amount of auxiliary glue (mg) | 13.3 | 13.3 | 13.3 | 13.3 | 13.3 | 13.3 | 0 | 0 |
| Relative difference (%) | +33% | +33% | +33% | +33% | +33% | +33% | Absent | Absent |

In this alternative, only zones Z7 and Z8 have no auxiliary glue.

In general, a fibrous thermoplastic layer (e.g. NW1151ZP hot-melt adhesive ex Fuller) may be uniformly sprayed at a basis weight of 5 gsm to cover the whole of the absorbent material deposition area, stopping for example at 5 mm from each transversal sides of the substrate (as illustrated in FIG. 1) to form an absorbent structure according to the invention.

The absorbent structure described above can be combined with a second absorbent structure having generally the same reparation of land areas and junction areas and adhesive application. The land areas of the each respective substrate may be combined with an offset of e.g. ca. 5 mm in the longitudinal direction so that land areas of one structure are centered on the junction areas of the other structure. This allows forming a combined substantially continuous absorbent material area. The second substrate may be wider (e.g. 165 mm) than the first substrate, so that transversally extending side flaps from the second substrate can be formed and folded around the longitudinal edges of the core and the external surface of the first substrate to form a C-wrap on the longitudinal sides of the core, with one or several thin line of adhesive applied longitudinally on the flaps to secure the seal. The transversal front and back ends of both substrates may be glued in face to face relation to form two transversal seals.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure comprising:
a substantially planar substrate extending in a transversal direction and a longitudinal direction,
an auxiliary glue applied directly over the substrate on an auxiliary glue application area,
an absorbent material comprising from about 80% to about 100% by weight of superabsorbent polymer particles deposited over the substrate on an absorbent material deposition area comprising a pattern of absorbent material land areas separated by absorbent material-free junction areas, wherein the absorbent material deposition area can be notionally divided into eight deposition zones of equal length along the longitudinal direction; and
a fibrous thermoplastic adhesive layer which covers at least some of the land areas and at least some of the absorbent material-free junction areas to thereby immobilize at least some of the absorbent material on the substrate;
wherein an amount of the absorbent material is profiled along the longitudinal direction of the structure so that at least one of the eight deposition zones is a zone of lower absorbent material amount having an amount of absorbent material that is at least 20% by weight lower than the average amount of absorbent material in the eight deposition zones, and the auxiliary glue is absent, or present at a level of at least 50% by weight lower than the average amount of auxiliary glue in the eight deposition zones, in at least one of these zones of lower absorbent material amount.

2. The absorbent structure of claim 1, wherein at least one of the eight deposition zones is a zone of higher absorbent material amount having an amount of absorbent material that is at least 20% higher than the average amount of absorbent material in the eight deposition zones and the auxiliary glue is present in at least one of these zones of higher absorbent material amount.

3. The absorbent structure of claim 1, wherein at least one zone of lower absorbent material amount is situated in the back third of the structure, as measured in the longitudinal direction.

4. The absorbent structure of claim 1, wherein the auxiliary glue is applied as a plurality of longitudinally-extending slots.

5. The absorbent structure of claim 4, wherein the plurality of longitudinally-extending slots have a transversal spacing there between of from about 0.5 mm to about 4 mm.

6. The absorbent structure of claim 5, wherein the slots have a width of from about 0.5 mm to about 3 mm.

7. The absorbent structure of claim 1, wherein the auxiliary glue application area has a surface which is no greater than about 80% the surface of the absorbent material deposition area.

8. The absorbent structure of claim 7, wherein the auxiliary glue application area has a surface which is no greater than about 70% of the surface of the absorbent material deposition area.

9. The absorbent structure of claim 1, wherein the auxiliary glue application area has a surface which is at least about 20% of the surface of the absorbent material deposition area.

10. An absorbent core comprising a first absorbent structure comprising
a substantially planar substrate extending in a transversal direction and a longitudinal direction,
an auxiliary glue applied directly over the substrate on an auxiliary glue application area,
an absorbent material comprising from about 80% to about 100% by weight of superabsorbent polymer particles deposited over the substrate on an absorbent material deposition area comprising a pattern of absorbent material land areas separated by absorbent material-free junction areas, wherein the absorbent material deposition area can be notionally divided into eight deposition zones of equal length along the longitudinal direction; and
a fibrous thermoplastic adhesive layer which covers at least some of the land areas and at least some of the absorbent material-free junction areas to thereby immobilize at least some of the absorbent material on the substrate;
wherein an amount of the absorbent material is profiled along the longitudinal direction of the structure so that at least one of the eight deposition zones is a zone of lower absorbent material amount having an amount of absorbent material that is at least 20% by weight lower than the average amount of absorbent material in the eight deposition zones, and the auxiliary glue is absent, or present at a level of at least 50% by weight lower than the average amount of auxiliary glue in the eight deposition zones, in at least one of these zones of lower absorbent material amount, and
a second substrate joined with the substrate of the first absorbent structure so that both substrates form a core wrap enclosing the absorbent material of the absorbent core.

11. The absorbent core of claim 10, the absorbent core comprising a second absorbent structure, the second absorbent structure comprising:
the second substrate,
a second absorbent material comprising from about 80% to about 100% by weight of superabsorbent particles and deposited over the second substrate in a pattern of absorbent material land areas separated by absorbent material-free junction areas,
a second fibrous thermoplastic adhesive layer arranged to cover at least some of the land areas and the absorbent material-free junction areas of the second absorbent material to thereby immobilize at least some of the second absorbent material on the second substrate;
wherein the first absorbent structure and the second absorbent structure are joined so that the first substrate and the second substrate form together a core wrap enclosing the first and second absorbent materials.

12. The absorbent core of claim 11, wherein the first absorbent structure and the second absorbent structure are joined together with the respective patterns of land areas and junction areas of the two absorbent structures being offset from each other so that the combined absorbent material layer is substantially continuous.

13. The absorbent core of claim 10, wherein the first substrate and the second substrate are sealed at the periphery of the core by at least one transversal end seal and/or at least one longitudinal side seal.

14. The absorbent core of claim 13, wherein the first substrate and the second substrate are sealed at the periphery of the core by at least one transversal end seal and/or at least one longitudinal side seal.

15. The absorbent core of claim 10, wherein at least one of the substrates is a nonwoven layer.

16. The absorbent core of claim 15, wherein the substrate comprises spunbond and meltblown component layers such as a SMS or SMMS nonwoven layer.

17. An absorbent article for personal hygiene, the article comprising:
 a liquid permeable topsheet;
 a liquid impermeable backsheet; and
 the absorbent structure of claim 1 between the topsheet and the backsheet.

18. A method of making the absorbent structure of claim 1, comprising the subsequent steps of:
 providing a substantially planar substrate;
 applying an auxiliary glue directly over the substrate on an auxiliary glue application area,
 depositing over the substrate an absorbent material comprising from about 80% to about 100% by weight of superabsorbent particles on an absorbent material deposition area comprising a pattern of material land areas separated by absorbent material-free junction areas, wherein the absorbent material deposition area can be notionally divided in eight deposition zones of equal length along the longitudinal direction of the structure;
 applying a fibrous thermoplastic adhesive layer on at least some of the land areas and the absorbent material-free junction areas to thereby immobilize at least some of the absorbent material on the substrate;
 wherein an amount of the absorbent material is profiled along the longitudinal direction of the structure so that at least one of the deposition zone, is a zone of lower absorbent material amount that has an amount of absorbent material that is at least 20% by weight lower than the average amount of absorbent material in the absorbent material deposition area, and the auxiliary glue is absent, or present at a level of at least 50% lower than the average amount of auxiliary glue in the eight zones, in at least one of these zones of lower absorbent material amount.

19. The method of making the absorbent structure of claim 18, further comprising the step of:
 joining the absorbent structure with a second substrate, so that the first substrate and second substrate form together a core wrap enclosing the absorbent material of the absorbent core.

* * * * *